(12) United States Patent (10) Patent No.: US 7,550,742 B2
Perry et al. (45) Date of Patent: Jun. 23, 2009

(54) UV LIGHT REDUNDANCY SYSTEM

(76) Inventors: Carlos Perry, 8142 Trail Timber Dr., Gainesville, VA (US) 20165; Richmond Way Perry, 9559 Tudor Oaks Dr., Manassas, VA (US) 20110

(*) Notice: Subject to any disclaimer, the term of this patent is extended or adjusted under 35 U.S.C. 154(b) by 234 days.

(21) Appl. No.: 11/771,385

(22) Filed: Jun. 29, 2007

(65) Prior Publication Data

US 2008/0006583 A1 Jan. 10, 2008

Related U.S. Application Data

(60) Provisional application No. 60/806,370, filed on Jun. 30, 2006.

(51) Int. Cl.
*A61L 9/20* (2006.01)

(52) U.S. Cl. .................................................... 250/436
(58) Field of Classification Search ................ 250/436, 250/435, 432 R
See application file for complete search history.

(56) References Cited

U.S. PATENT DOCUMENTS 4,103,167 A * 7/1978 Ellner .................... 250/432 R

* cited by examiner

*Primary Examiner*—Kiet T Nguyen
(74) *Attorney, Agent, or Firm*—Greenblum & Bernstein, P.L.C.

(57) ABSTRACT

An effluent treatment control system comprising a sensor that determines when a primary ultraviolet lamp disposed in a first flow path of an effluent fails. The system also includes a controller that, upon receiving a signal from the sensor, automatically turns on a backup ultraviolet lamp disposed in a second flow path of the effluent.

20 Claims, 4 Drawing Sheets

UV LIGHT REDUNDANCY SYSTEM

CROSS REFERENCE TO RELATED APPLICATIONS

This application claims priority under 35 U.S.C. §119 to U.S. Provisional Application No. 60/806,370 filed on Jun. 30, 2006, the contents of which are incorporated herein by reference in their entirety.

BACKGROUND OF THE INVENTION

1. Field of the Invention

The invention generally relates to an ultraviolet (UV) light disinfection system, and, more particularly, to a control system for a redundancy system which is used in a UV light disinfection system.

2. Discussion of Background Information

Wastewater can be treated with a disinfection unit which is a system that kills disease-causing microorganisms in wastewater, and is used when discharge on the surface is permitted. In one conventional implementation, ultraviolet (UV) light systems are used to treat good quality effluent, such as that from properly functioning aerobic units and sand filters. Additionally, UV light systems are applicable to any water treatment or purification, including, for example, home use for well water and anywhere soil may not percolate.

More specifically, UV water purification lamps take advantage of wavelength properties that can be used to disinfect water. UV light eliminates a wide range of contaminants from a water supply. For example, UV light is effective against bacteria, viruses, algae, molds and yeasts, and disease causing oocysts.

UV water purification lamps are susceptible to failure. Such failure may lead to the undesirable effect of water going untreated. Periodic inspections of UV lamp water purification system are commonly used to guard against such failure. Inspections, however, are costly both in terms of time and money. Moreover, periodic inspections still allow water to go untreated if a lamp fails between scheduled inspections.

Accordingly, there exists a need in the art to overcome the deficiencies and limitations described hereinabove.

SUMMARY OF THE INVENTION

In a first aspect of the invention, there is an effluent treatment control system comprising a sensor that determines when a primary ultraviolet lamp disposed in a first flow path of an effluent fails. The system also includes a controller that, upon receiving a signal from the sensor, automatically turns on a backup ultraviolet lamp disposed in a second flow path of the effluent.

The sensor may comprise a current sensor operable to sense when the primary ultraviolet lamp is not drawing current. The controller may comprise a programmable logic controller that, upon receipt of the signal from the current sensor, causes a switch to supply power to the backup ultraviolet lamp.

The sensor may comprise a light sensor operable to sense when the primary ultraviolet lamp is not emitting light. The controller may comprise a programmable logic controller that, upon receipt of the signal from the light sensor, causes a switch to supply power to the backup ultraviolet lamp.

The system may further comprise an alarm, whereby the controller activates the alarm upon the supplying of power to the backup ultraviolet lamp. The alarm may comprise a visual indicator.

The primary ultraviolet lamp and the backup ultraviolet lamp may be disposed in a casing. The casing may comprise: an inlet arranged to receive an effluent; a first chamber constituting the first flow path for the effluent and in which the primary ultraviolet lamp is arranged; a second chamber constituting the second flow path for the effluent and in which the backup ultraviolet lamp is arranged; an outlet arranged to discharge the effluent from the casing; and a flow diversion plate between the inlet and the outlet. The casing may be structured and arranged for use in a pressurized effluent line or a gravity flow line.

The system may further comprise a control panel housing the controller and the sensor, a master power disconnect, and a dual wiring harness operatively connecting the controller to the primary ultraviolet lamp and the backup ultraviolet lamp. Additionally, the system may include a conduit extending between the control panel to the primary ultraviolet lamp and the backup ultraviolet lamp, wherein the dual wiring harness is arranged inside the conduit.

In another aspect of the invention, there is an ultraviolet light redundancy control system comprising a controller operatively connected between: (i) an electrical power source and (ii) a primary ultraviolet lamp disposed in a first flow path of an effluent and a backup ultraviolet lamp disposed in a second flow path of the effluent. The system further comprises a sensor arranged to sense when the primary ultraviolet lamp fails. The controller automatically turns on the backup ultraviolet lamp upon receipt of a signal from the sensor that the primary ultraviolet lamp has failed. Moreover, the system may further comprise an alarm that is activated by the controller when the backup ultraviolet lamp is turned on.

In another aspect of the invention, there is a method for providing an ultraviolet light redundancy system for treating effluent. The method includes providing control to illuminate a primary ultraviolet lamp disposed in a first flow path of an effluent; sensing when the a primary ultraviolet lamp fails; and, upon the sensing, automatically providing control to illuminate a backup ultraviolet lamp disposed in a second flow path of the effluent. The method may further comprise generating an alarm upon the sensing.

BRIEF DESCRIPTION OF THE DRAWINGS

The invention is described in the detailed description which follows, in reference to the noted plurality of drawings by way of non-limiting examples of exemplary embodiments of the invention, in which like reference numerals represent similar parts throughout the several views of the drawings, and wherein.

DETAILED DESCRIPTION OF EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The invention is directed to a UV light redundancy system. In embodiments, a water purification system comprises at least one primary UV lamp, at least one backup UV lamp, and a controller that is arranged to automatically turn on the backup UV lamp when the primary UV lamp fails. In this manner, the invention ensures that a redundant UV light or secondary bulb provides protection when the primary bulb fails. In embodiments, the system is also equipped with an alarm that notifies the user of a bulb failure.

Figure 1:
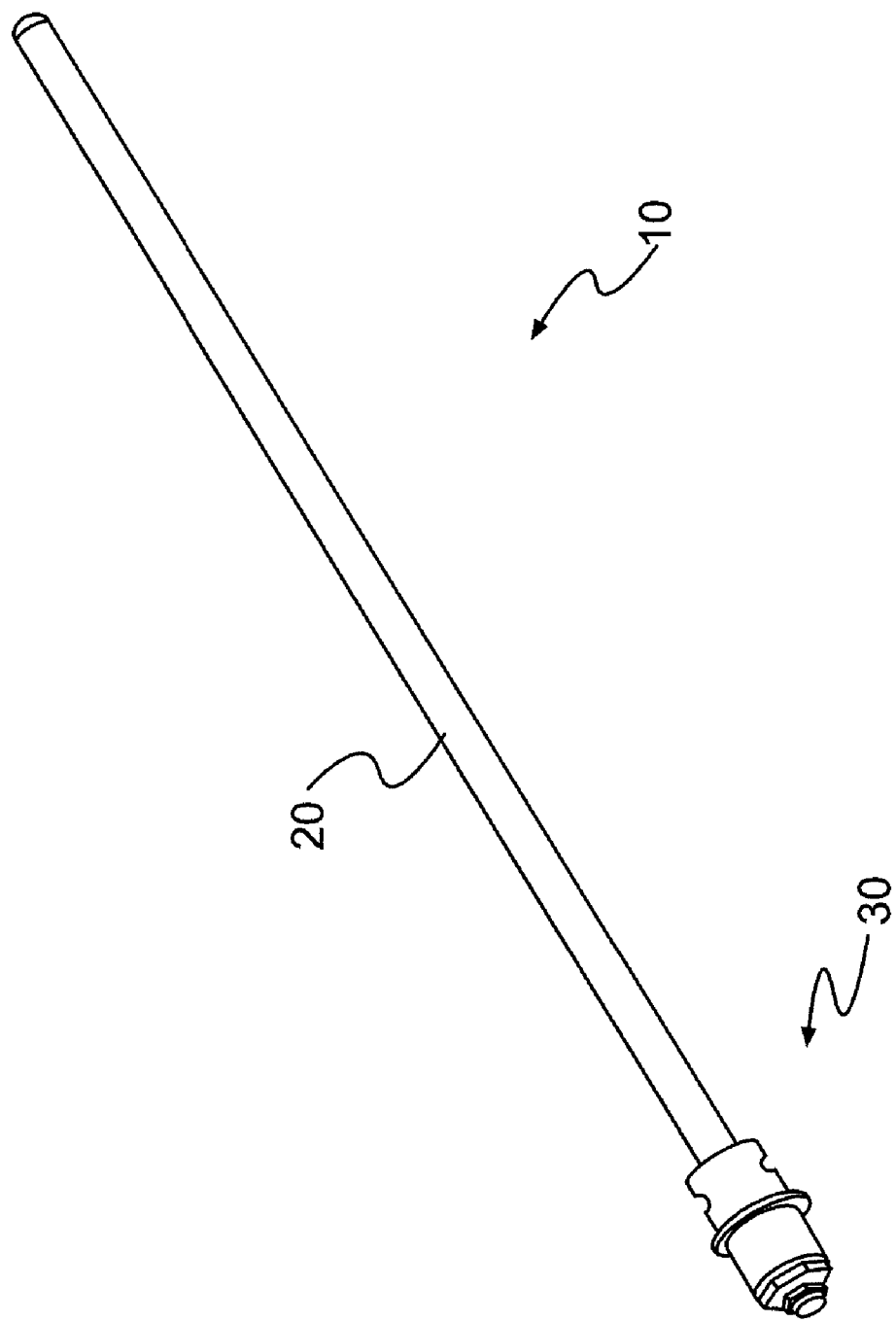
FIG. 1 shows a lamp assembly according to aspects of the invention.

FIG. 1 shows a lamp assembly 10 that can be used as a primary lamp and/or a backup lamp according to aspects of the invention. The lamp assembly 10 comprises a UV light bulb 20, such as, for example, a UV light bulb manufactured by Atlantic Ultraviolet Corporation of Hauppauge, N.Y., although any suitable UV light bulb may be used with the invention. The lamp assembly 10 also includes a connector 30 structured and arranged to provide an electrical connection to the light bulb 20. In embodiments, the connector 30 is also structured and arranged to connect the lamp assembly 10 to a water purification casing (described in greater detail below).

Figure 2:
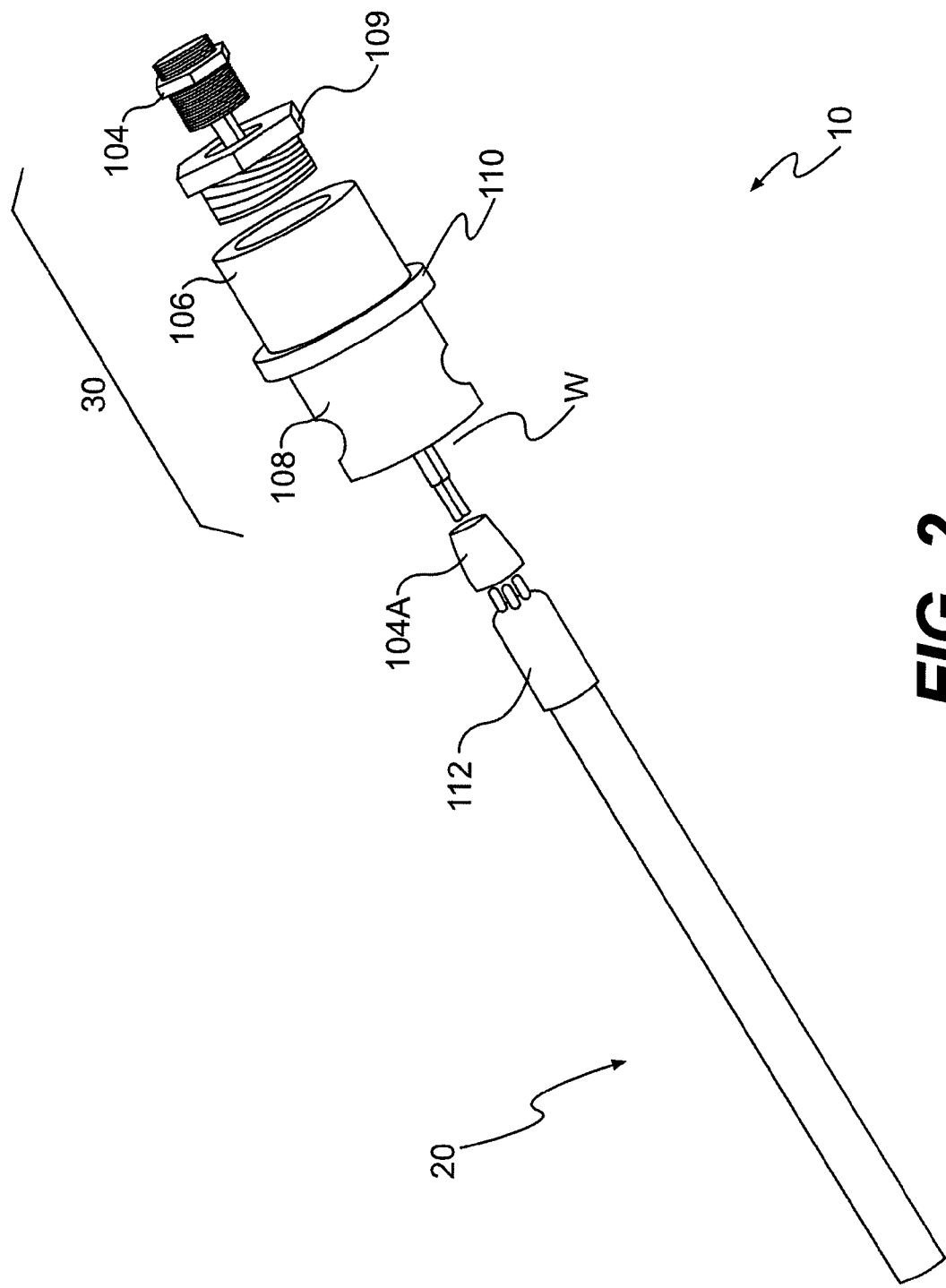
FIG. 2 shows an exploded view of a lamp assembly according to aspects of the invention.

FIG. 2 shows an exploded view of a lamp assembly 10 according to aspects of the invention. In embodiments, the connector 30 may include a housing 106 having a flange 110 and cam receiving portion 108. The cam receiving portion 108 is shown to be a groove about the entire circumference of its main housing portion, such that the connector 30 may be locked into a casing, as described in greater detail below. The connector 30 further includes a reducer portion 109 having a threaded connection with the housing 106 and a socket 104. The socket 104, for example, includes a four-prong adapter 104a electrically connectable to an electrical connection portion 112 of the UV light bulb 20. The four-prong adapter 104a is electrically connected to a tapered two pole connector via wires W.

Figure 3:
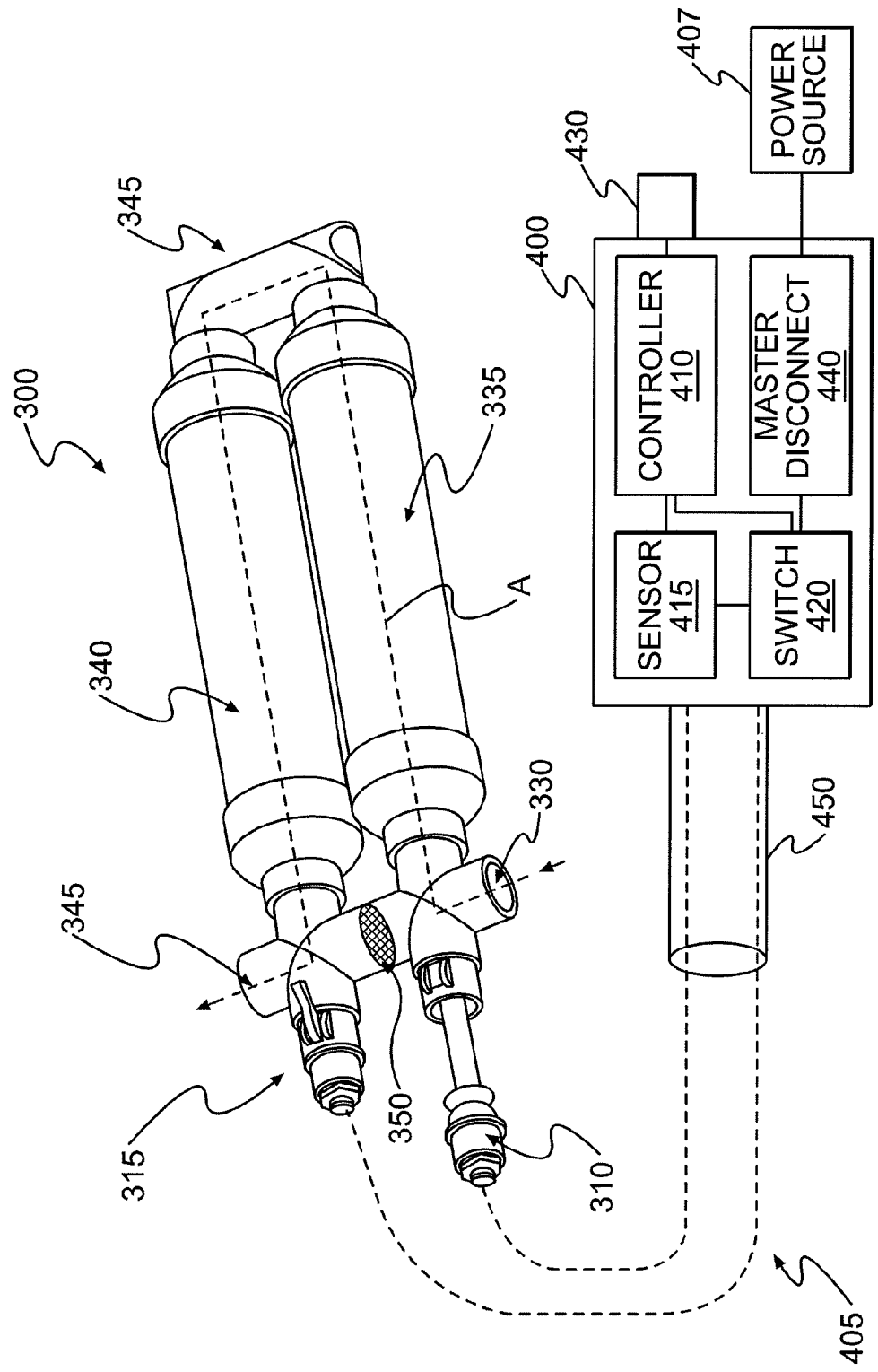
FIG. 3 shows a redundancy system according to aspects of the invention.

FIG. 3 shows a redundancy system according to aspects of the invention. The system includes a casing 300 through which effluent passes. At least one primary UV lamp 310 and at least one backup UV lamp 315 are arranged in the casing 300. The primary and backup UV lamps 310, 315 may each comprise, for example, a lamp assembly 10, as described above with respect to FIGS. 1 and/or 2. The primary and backup UV lamps 310, 315 may be connected to the casing 300 in any suitable manner, such as, for example, by using the locking and disconnect system described in U.S. patent application Ser. No. 11/537,473, the disclosure of which is incorporated herein by reference in its entirety. To demonstrate aspects of the invention, the primary UV lamp 310 is shown partially removed from the casing 300 in FIG. 3; however, in operation, the primary UV lamp 310 may be fully inserted into the casing 300, similar to the depiction of the backup UV lamp 315.

In embodiments, the casing 300 includes an inlet 330 arranged to receive effluent, a first chamber 335 downstream of the inlet 330, a second chamber 340 downstream of the first chamber 335, and an outlet 345 arranged to discharge effluent downstream of the second chamber 340. An elbow 345, or any other suitable connection, may be used to connect the first chamber 335 and the second chamber 340. Moreover, a flow diversion plate 350, or any other suitable seal, may be used to separate the inlet 330 an the outlet 345. In this manner, a flow path "A" extends serially from the inlet 330, to the first chamber 335, the second chamber 340, and the outlet 345, as depicted in FIG. 3.

In implementations, the primary UV lamp 310 is arranged at least partially inside the first chamber 335 and the backup UV lamp 315 is arranged at least partially inside the second chamber 340. In a preferred embodiment, the primary UV lamp 310 extends inside the first chamber 335 for substantially the entire length of the first chamber 335, and the backup UV lamp 315 is extends inside the second chamber 340 for substantially the entire length of the second chamber 340. Accordingly, effluent passing through the first chamber 335 may be exposed to UV light when the primary UV lamp 310 is energized (i.e., turned on), and effluent passing through the second chamber 340 may be exposed to UV light when the backup UV lamp 315 is energized. In this manner, effluent may be treated with UV light inside at least one chamber 335, 340.

Although the primary UV lamp 310 is shown adjacent the inlet 330 and the backup UV lamp 315 is shown adjacent the outlet 345, it is noted that the invention is not limited to such a configuration. That is to say, the primary UV lamp 310 may be arranged adjacent the outlet and the backup UV lamp 315 may be arranged adjacent the inlet. Moreover, the invention is not limited to the use of a single primary UV lamp 310 and a single backup UV lamp 315. For example, any suitable number of primary UV lamps and any suitable number of backup UV lamps may be used within the scope of the invention.

Furthermore, the bulb portions of the respective lamps 310, 315 may be housed in a water tight protective sleeve to protect the bulb. In such an embodiment, the sleeve and bulb are easily removed by a locking and disconnect system described in U.S. patent application Ser. No. 11/537,473 for cleaning or replacement.

The chambers 335, 340 as well as the inlet 330, outlet 345 and other features of the casing 300 may be of any size and shape suitable for water applications such as wastewater treatment systems, to name but one type of application. The various features of the casing 300 may be sized and shaped to achieve any suitable flow rate of effluent, such as, for example, about 10 gallons/minute, although other flow rates may be used with the invention. The system can be used in a pressurized effluent line or in a gravity flow line.

Moreover, the casing 300 may be made of any suitable material. For example, portions of the casing 300 may be made of polyvinyl chloride (PVC) piping, preferably schedule 80 PVC piping. Additionally, the PVC piping may be treated with ultraviolet inhibitors to prevent PVC degradation during exposure to UV light. Alternatively, the casing 300 may be made of stainless steel, or other metal or alloy, and may utilize the reflective properties of the material to further enhance treatment of the effluent.

Still referring to FIG. 3, the redundancy system further comprises a control 400 operatively connected to the primary and backup UV lamps 310, 315. In embodiments, the control 400 may be any suitable control system that is structured and arranged to selectively apply electrical power to the primary and backup UV lamps 310, 315. For example, a dual lamp wiring harness 405 may electrically connect the control 400 to the primary and backup UV lamps 310, 315, respectively. Moreover, the control 400 may be electrically connected to an electrical power source 407, such as, for example, a 120 volt AC outlet. Accordingly, the control 400 may selectively apply electrical power to the respective lamps 310, 315.

In embodiments, the control 400 comprises a controller 410, a sensor 415, and a switch 420. The controller 410 may comprise, for example, a programmable logic controller (PLC). The sensor 415 may comprise, for example, a current sensing relay that provides a signal to the controller 410 when the primary UV lamp 310 is not drawing current (i.e., is not energized). When the controller 410 receives a signal from the sensor 415 that the primary UV lamp is not functioning, the controller 410 causes the switch 420 to provide electrical power to the backup UV lamp 315. In this manner, the system automatically turns on the backup UV lamp 315 when the primary UV lamp 310 fails. Although a PLC and current sensing relay have been described, the invention is not limited to these embodiments, and other suitable types of controllers and sensors may be used within the scope of the invention. For example, instead of a current sensing relay, the sensor 415 may comprise a light sensor disposed inside the casing that senses whether the primary UV lamp 310 is emitting light or not.

In implementations, the control 400 further comprises an alarm 430. For example, the alarm 430 may comprise an indicator light that is energized by the controller 410 when the primary UV lamp 310 fails. In embodiments, the alarm 430 is arranged on the control 400. By arranging the alarm 430 outside of the confines of the casing 300, a user can see a visual indication of the operational status of the primary UV lamp 310 without having to disassemble and/or remove the primary UV lamp 310 from the casing.

Additionally or alternatively, the controller 410 may send a message to any known computing device when the primary UV lamp 310 fails. For example, the controller 410 may comprise a central processing unit (CPU) connected to a communication network, whereby the CPU sends an email to another computing device on the communication network when the primary UV lamp 310 fails.

Still referring to FIG. 3, the control 400 may further comprise a master power disconnect 440 that is operable to interrupt the electrical power to the lamps 310, 315. For example, the master power disconnect 440 may comprise an ON/OFF switch that selectively opens and closes a circuit between the electrical power source 407 and the lamps 310, 315. In this manner, a user may turn off the power to the lamps 310, 315 during handling of the casing (e.g., during bulb replacement).

In embodiments, the control 400 is mounted on any suitable structure within a predetermined distance (e.g., six feet) of the casing 300. A conduit 450 (shown only partially in FIG. 3) may be provided between the control 400 and the casing 300 for shielding electrical wires (e.g., the dual lamp wiring harness 405) extending between the control 400 and the casing 300. The control 400 may comprise, for example, a 12.5" by 17.5" by 8" box that houses the controller 410, sensor 415, and switch 420, and upon an external surface of which the alarm 430 is arranged. Moreover, the conduit 450 may comprise, for example, a 1.5" diameter electrical wire conduit.

Figure 4:
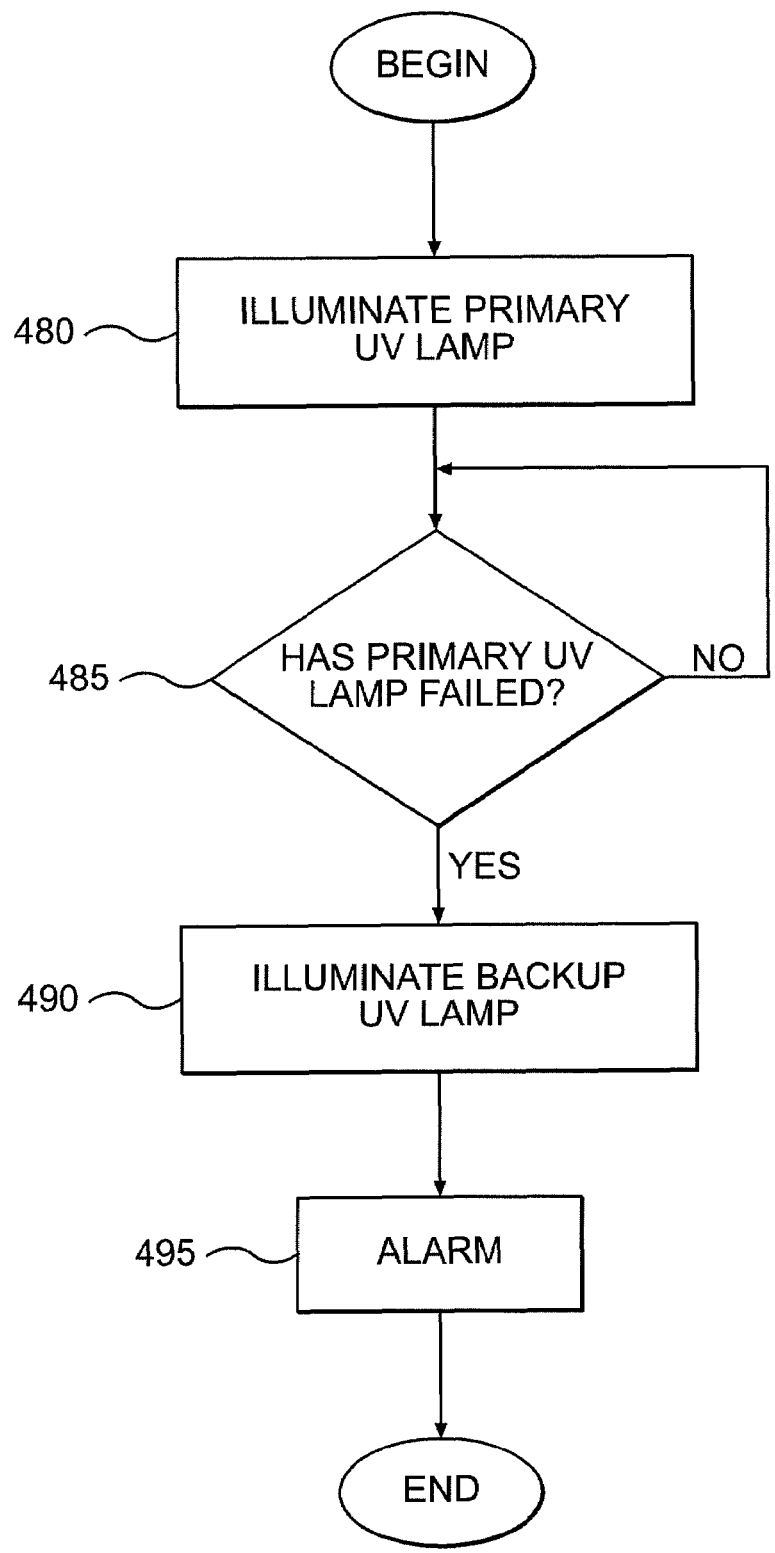
FIG. 4 shows a flow diagram depicting an implementation of a method according to aspects of the invention.

FIG. 4 shows a flow diagram depicting an implementation of a method according to aspects of the invention. The steps may be executed by any suitable computing device, and programming for causing the steps to be executed may be stored in any suitable computer readable medium. At step 480, a primary UV lamp is energized. In embodiments, this comprises applying electrical power to a UV lamp in a effluent treatment system, such as the primary UV lamp and casing described above with respect to FIG. 3.

At step 485, a determination is made as to whether the primary UV lamp is functioning properly. In embodiments, the determination may be made with a sensor and controller, such as those described above with respect to FIG. 3. When the primary UV lamp is functioning properly, the process loops back to repeat determining whether the primary UV lamp is functioning properly, such that a substantially continuous monitoring process is provided.

When the primary UV lamp is not functioning properly (e.g., is not illuminated), the process proceeds to step 490 where the backup UV lamp is energized. In embodiments, this is accomplished via a controller and switch, such as those described above with respect to FIG. 3. Additionally, yet optionally, an alarm may be activated at step 495. The alarm may comprise an indicator light, such as that described above with respect to FIG. 3.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. An effluent treatment control system, comprising:
    a sensor that determines when a primary ultraviolet lamp disposed in a first flow path of an effluent fails; and
    a controller that, upon receiving a signal from the sensor, automatically turns on a backup ultraviolet lamp disposed in a second flow path of the effluent.

2. The effluent treatment control system of claim 1, wherein the sensor comprises a current sensor operable to sense when the primary ultraviolet lamp is not drawing current.

3. The effluent treatment control system of claim 2, wherein the controller comprises a programmable logic controller that, upon receipt of the signal from the current sensor, causes a switch to supply power to the backup ultraviolet lamp.

4. The effluent treatment control system of claim 3, further comprising an alarm, wherein the controller activates the alarm upon the supplying of power to the backup ultraviolet lamp.

5. The effluent treatment control system of claim 4, wherein the alarm comprises a visual indicator.

6. The effluent treatment control system of claim 1, wherein the sensor comprises a light sensor operable to sense when the primary ultraviolet lamp is not emitting light.

7. The effluent treatment control system of claim 6, wherein the controller comprises a programmable logic controller that, upon receipt of the signal from the light sensor, causes a switch to supply power to the backup ultraviolet lamp.

8. The effluent treatment control system of claim 7, further comprising an alarm, wherein the controller activates the alarm upon the supplying of power to the backup ultraviolet lamp.

9. The effluent treatment control system of claim 8, wherein the alarm comprises a visual indicator.

10. The effluent treatment control system of claim 1, wherein the primary ultraviolet lamp and the backup ultraviolet lamp are disposed in a casing.

11. The effluent treatment control system of claim 10, wherein the casing comprises:

an inlet arranged to receive the effluent;

a first chamber constituting the first flow path and in which the primary ultraviolet lamp is arranged;

a second chamber constituting the second flow path and in which the backup ultraviolet lamp is arranged;

an outlet arranged to discharge the effluent from the casing; and a flow diversion plate between the inlet and the outlet.

12. The effluent treatment control system of claim 11, wherein the casing is structured and arranged for use in a pressurized effluent line or a gravity flow line.

13. The effluent treatment control system of claim 1, further comprising a control panel housing the controller and the sensor.

14. The effluent treatment control system of claim 13, further comprising a master power disconnect.

15. The effluent treatment control system of claim 13, further comprising a dual wiring harness operatively connecting the controller to the primary ultraviolet lamp and the backup ultraviolet lamp.

16. The effluent treatment control system of claim 15, further comprising a conduit extending between the control panel to the primary ultraviolet lamp and the backup ultraviolet lamp, wherein the dual wiring harness is arranged inside the conduit.

17. An ultraviolet light redundancy control system, comprising:

a controller operatively connected between: (i) an electrical power source and (ii) a primary ultraviolet lamp disposed in a first flow path of an effluent and a backup ultraviolet lamp disposed in a second flow path of the effluent; and a sensor arranged to sense when the primary ultraviolet lamp fails, wherein the controller automatically turns on the backup ultraviolet lamp upon receipt of a signal from the sensor that the primary ultraviolet lamp has failed.

18. The ultraviolet light redundancy control system of claim 17, further comprising an alarm that is activated by the controller when the backup ultraviolet lamp is turned on.

19. A method for providing an ultraviolet light redundancy system for treating effluent, comprising:

providing control to illuminate a primary ultraviolet lamp disposed in a first flow path of an effluent;

sensing when the primary ultraviolet lamp fails; and upon the sensing, automatically providing control to illuminate a backup ultraviolet lamp disposed in a second flow path of the effluent.

20. The method of claim 19, further comprising generating an alarm upon the sensing.

* * * * *